Figure 1B:
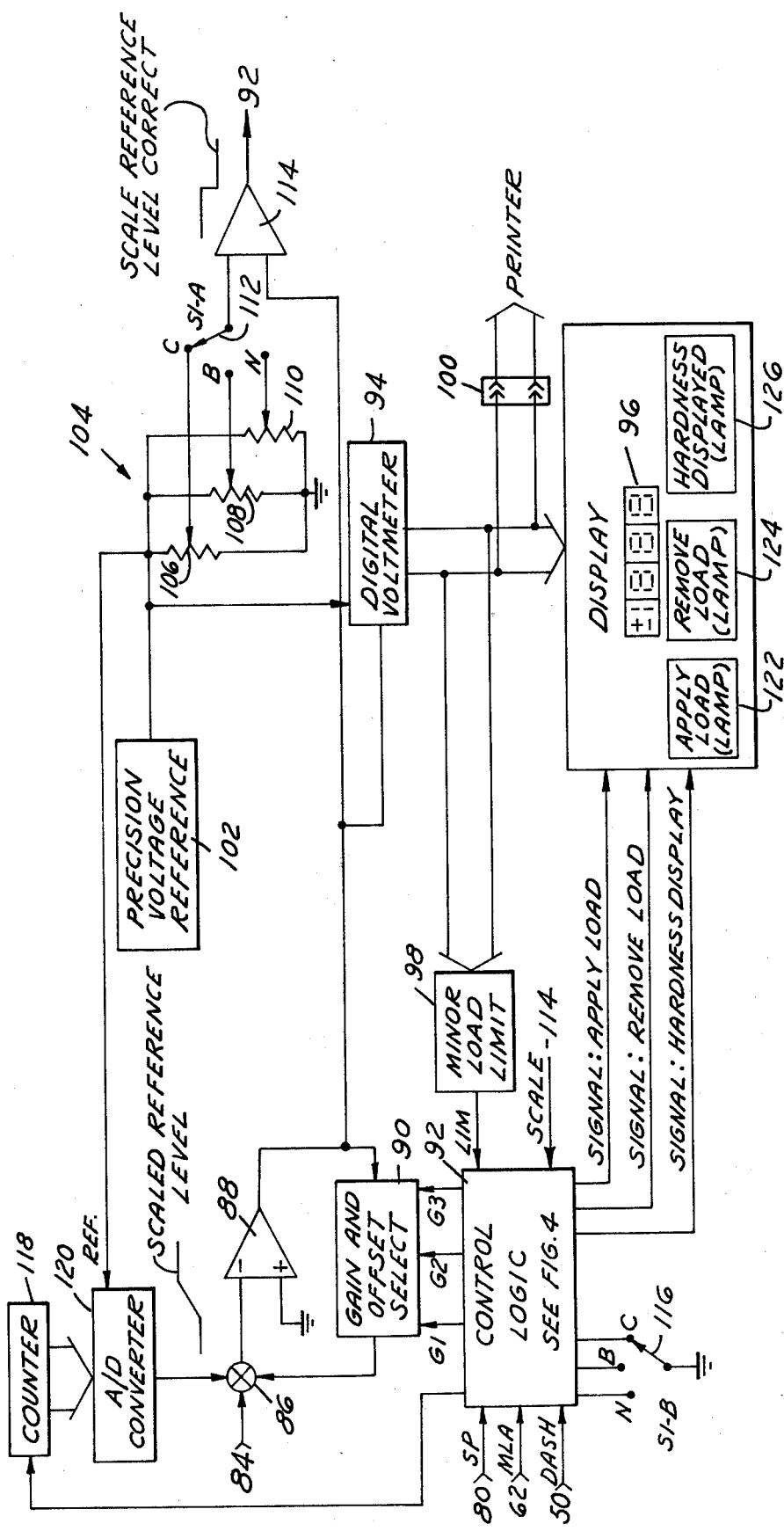

United States Patent [19]

Fohey

[11] 4,182,164

[45] Jan. 8, 1980

[54] PENETRATION HARDNESS TESTER WITH DIGITAL READOUT

[75] Inventor: Donald R. Fohey, Plymouth, Mich.

[73] Assignee: K. J. Law Engineers, Inc., Farmington Hills, Mich.

[21] Appl. No.: 943,315

[22] Filed: Sep. 18, 1978

[51] Int. Cl.$^2$ ............................................. G01N 3/48
[52] U.S. Cl. ...................................................... 73/83
[58] Field of Search .......................... 73/83, 81, 82, 85

[56] References Cited

U.S. PATENT DOCUMENTS

| 2,554,206 | 5/1951 | Pearson et al. | 73/83 |
| 2,858,696 | 11/1958 | Underwood | 73/83 |
| 3,590,630 | 7/1971 | Ericksson | 73/83 |

Primary Examiner—Jerry W. Myracle
Attorney, Agent, or Firm—Barnes, Kisselle, Raisch & Choate

[57] ABSTRACT

A semi-automatic penetration hardness tester for measuring hardness of a test specimen in a selected one of a number of hardness number scales. A digital display indicates penetrator displacement during application of a minor load in a first mode of operation and may be monitored by an operator to achieve a penetrator displacement within a preselected range corresponding to application of a minor load of desired magnitude. A control circuit senses manual initiation of a major load application and automatically scales the minor load penetrator reference position to a reference hardness number corresponding to and correlated with the selected hardness number scale. The control circuit also senses an operator error during the test procedure and automatically aborts the test.

28 Claims, 6 Drawing Figures

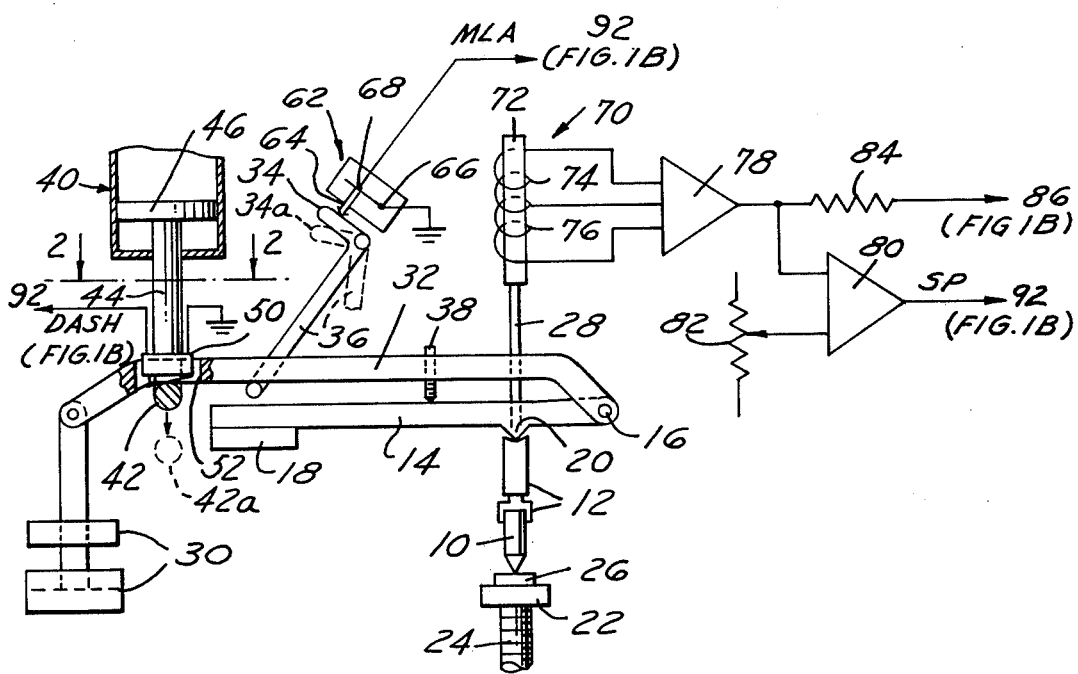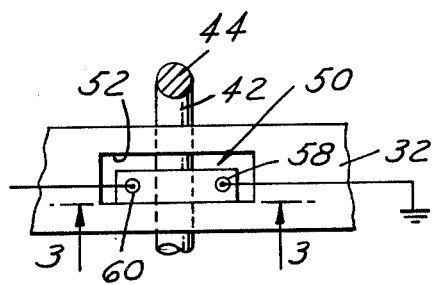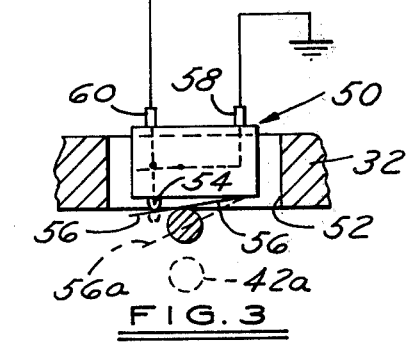
FIG.1A
FIG.2
FIG.3

PENETRATION HARDNESS TESTER WITH DIGITAL READOUT

The present invention is directed to penetration hardness testers, and more particularly to a semi-automatic hardness tester for providing a digital reading of specimen hardness number measured in one a plurality of selectable hardness scales.

Penetration hardness testers are well known in the art, and generally include a diamond- or ball-tip penetrator and means for successively applying minor and major loads of predetermined magnitude through the penetrator to a test specimen. A typical manual penetration hardness tester includes a lead screw for manually displacing a test specimen against a penetrator under minor load and a dial indicator for indicating a predetermined displacement of the penetrator corresponding to application of a minor load of desired magnitude. The minor load position is then to be made a reference position by manual adjustment of the indicator dial. A lever is provided for manual application of a major load, full major load being indicated to an operator when rotation of the indicator needle from the reference position ceases. The major load should then be removed and the final position of the dial indicator read as a determination of specimen hardness number.

Instruments of the foregoing type include several sources of inaccuracy and error. For example, although incorrect application of the minor load may result in substantial test inaccuracy, no provision is made for determining such incorrect application and/or for aborting the test as a result thereof. Inaccurate manual adjustment at the minor load position will result in substantial error since hardness number is determined as a measure of penetrator displacement between the first position after the major load is removed and the reference-minor load position. Similarly, an operator may accidently or intentionally substantially alter the final test result by removing the major before the indicator dial has ceased rotation. Moreover, a dial indicator reading often requires interpolation between indicator graduations. Digital penetration hardness testers have been previously proposed to overcome the latter difficulty. However, these devices do not, in general, overcome the other above-noted difficulties and sources of error in prior art penetration hardness testers.

Accordingly, a general object of the present invention is to provide a penetration hardness tester which is semi-automatic in operation, and which overcomes some or, preferably, all of the foregoing difficulties with prior art techniques. More specific objects of the present invention are to provide a penetration hardness tester which senses correct application of a minor test load, which automatically aborts further testing if such minor load is incorrectly applied, which yields a positive indication that a major test load has been fully applied, which aborts further testing if the major load is removed before fully applied to the penetrator and test specimen, which provides an accurate digital reading of hardness number in one of a plurality of selectable hardness scales, and/or in a preferred semi-automatic embodiment provides a step-by-step indication to an operator that he may proceed to the next stage of operation.

Figure 4:
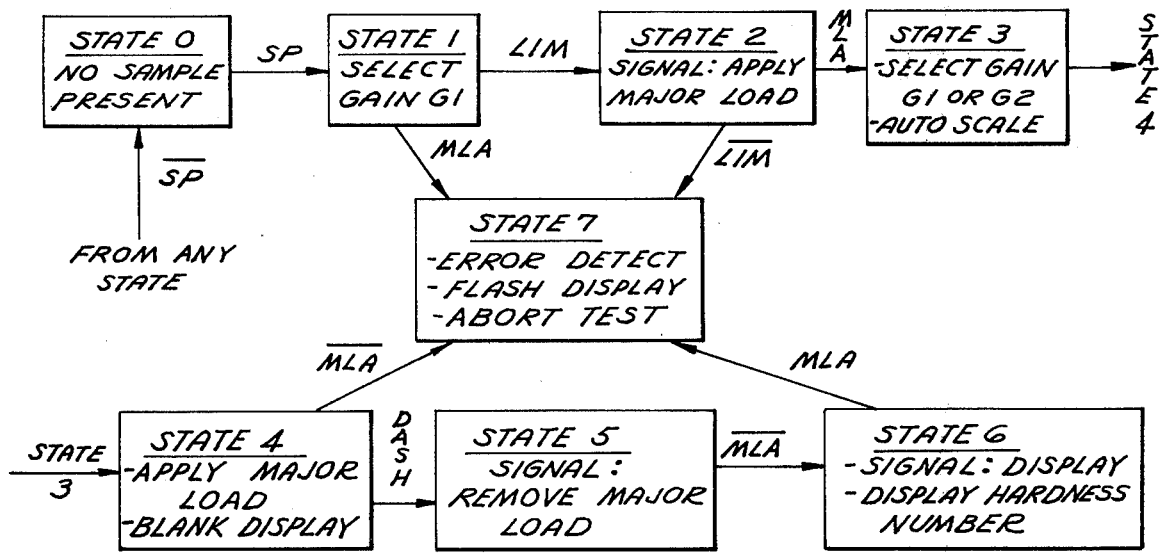
Figure 5:
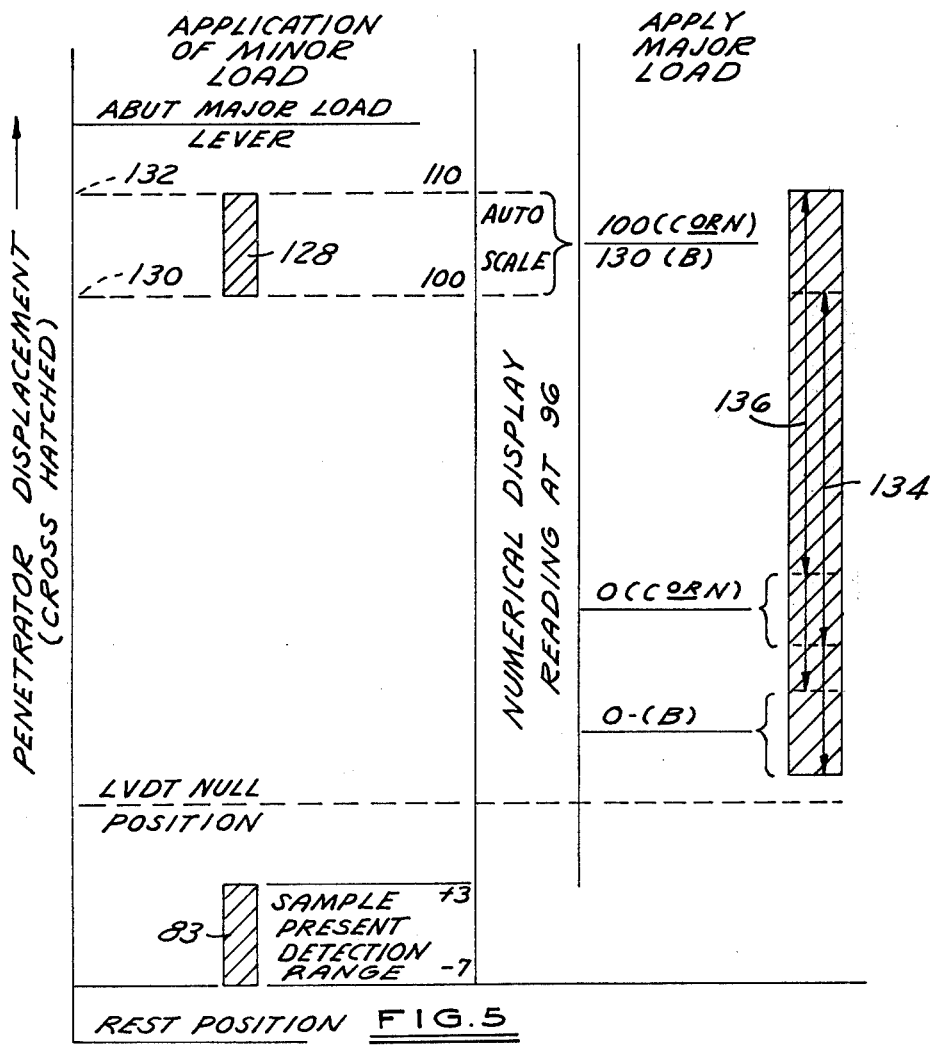

The invention, together with additional objects, features and advantages thereof, will be best understood from the following description, the appended claims, and the accompanying drawings in which:

FIGS. 1A and 1B are semi-schematic and semi-functional block diagrams which together illustrate a presently preferred embodiment of the semi-automatic penetration hardness tester provided by the invention;

FIGS. 2 and 3 are sectional views taken along the respective lines 2—2 in FIG. 1A and 3—3 in FIG. 2;

FIG. 4 is a state diagram which illustrates operation of the control logic circuit shown in FIG. 1B; and FIG. 5 is a graphic illustration useful in understanding operation of the invention.

The general theory of penetration hardness testing is well understood in the metallurgical arts. Generally, the standard test methods involve the use of ball- or diamond-tip penetrators and major and minor load of defined magnitudes. Specimen hardness is most often expressed in so-called Rockwell hardness numbers in one of a plurality of defined scales, such as the C or B hardness scale or the N superficial hardness scale. The Rockwell-type testing method is defined in detail in American Society for Testing and Materials publication E1-8-74. The background theory of penetration hardness testing need not be discussed herein except to the extent necessary to illustrate operation of the invention.

Referring to FIGS. 1A, 2 and 3, the mechanical portion of the penetration hardness tester in accordance with the invention includes a diamond- or ball-tip penetrator 10 replaceably carried in a holder 12 and vertically suspended within an enclosure (not shown). A lever arm 14 is pivitol in a vertical plane about a horizontal pin 16 and includes at its pivot-remote end a minor load weight 18 for applying a minor load of desired magnitude to penetrator 10 through a knife edge 20. The surrounding enclosure includes suitable means (not shown) for supporting penetrator 10 in a lower rest position against the weight of arm 14. An anvil 22 is carried by a lead screw 24 for supporting a test specimen 26 and for manually displacing such test specimen upwardly against penetrator 10 and the weight of minor load lever 14 to apply a minor load to the test specimen through the penetrator. A shaft 28 extends through lever arm 14 for providing an indication of penetrator displacement.

A plurality of selectable weights 30 are suspended from one end of a major load lever 32 which extends above minor load lever 14 and is pivotal in a vertical plane about pin 16. An operator handle 34 is carried externally of the surrounding enclosure (not shown) and normally supports major load lever 32 out of vertical engagement with lever 14 by means of the linkage illustrated schematically at 36. Upon manual pivotal displacement of handle 34 to the position illustrated in phantom at 34a, the major load lever 32 is permitted to engage the minor load lever through an adjustable screw 38. A dashpot generally indicated at 40 includes a piston 46 connected by a rod 44 to a linkage element 42 disposed beneath the pivot-remote end of lever 32 for supporting the lever and gradually lowering the lever to apply the major load through lever 14 and penetrator 10 to test specimen 26. As the major load is gradually assumed by the penetrator and test specimen, the proportion of such load carried by linkage 42 decreased until the entire major load is supported by the penetrator and test specimen. The linkage will then move further downwardly out of engagement with the major load lever to the position illustrated at 42a in FIGS. 1A and 3.

The mechanism of FIGS. 1A, 2 and 3 to the extent thus far described generally comprises a conventional manual hardness tester and may be purchased from a number of manufactures including specifically Officene Galileo of Florence, Italy. The particular penetration hardness tester with which the presently preferred embodiment of the invention may be utilized is the model D-300 tester marketed by Officene Galileo, and includes interchangeable diamond- and ball-tip penetrators 10, switch selectable minor load weights 18 and switch selectable major load weights 30 for C, B and N hardness scales.

In accordance with a first important aspect of the present invention, the mechanical portion of a conventional tester is modified by adding thereto an electrical switch 50 for providing a positive indication that the dashpot linkage 42 has dropped out of engagement with the major load lever 32, and thereby indicating that the entire major load has been applied to the penetrator and test specimen. More specifically, switch 50 comprises a conventional subminiature limit switch mounted in an opening 52 in lever arm 32, and having a switch actuator 54 and a pivotal actuator 56 projecting downwardly therefrom for engagement with linkage 42. One normally open switch terminal 58 is connected to electrical ground such that the second normally open terminal 60 is effectively connected to ground when actuator 54 and actuator arm 56 are urged upwardly by engagement with linkage 42. However, when linkage 42 drops to the disengaged position illustrated at 42a and actuator arm 56 assumes the normal position illustrated at 56a, the switch terminal 60 is effectively ungrounded or open and provides a DASH signal to the control electronics illustrated in FIG. 1B.

The mechanical portion of the hardness tester is further modified in accordance with the present invention by locating a second electrical limit switch 62 (FIG. 1A) adjacent the major load operator handle 34 such that the switch actuator 64 is depressed when the handle 34 is in the normal position and is released when the handle moves to the load-applying position illustrated at 34a. Normally open switch contacts 66,68 are respectively connected to electrical ground and to the control electronics of FIG. 1B to provide a ground signal when actuator 64 is depressed and the contacts are closed, and an open or ungrounded major load applied signal MLA when handle 34 is manually rotated toward position 34a. A penetrator position transducer comprising an LVDT 70 comprises a core 72 of magnetic material coupled to shaft 28 and a pair of differentially-connected coils 74,76 for sensing the position of core 72. Coils 74,76 are connected to a differential amplifier 78 which provides an analog d.c. output signal which decreases in magnitude as core 72 is displaced vertically upwardly. The output of amplifier 78 is connected to a second differential amplifier 80 which receives a reference input from an adjustable resistor 82. Resistor 82 is factory adjusted such that amplifier 80 senses a slight upward displacement of the penetrator from the rest position to provide a sample present signal SP to the control electronics of FIG. 1B. The sample present detection range 83 illustrated in FIG. 5 depends upon circuit parameters and is well below the LVDT null position.

The analog output of amplifier 78 is also connected through a resistor 84 to a summing junction 86 (FIG. 1B) at the inverting input of an operational amplifier 88 which has its non-inverting input connected to ground. Amplifier 88 provides an analog d.c. output signal which is inversely proportional to the sum of the signals at junction 86, and which therefore increases with upward penetrator movement. The output of amplifier 88 is looped back to input summing junction 86 through amplifier gain and offset selection circuit 90 which receives control signals for selecting gains G1, G2 or G3 from a control logic circuit 92. As will be explained in greater detail hereinafter, gain G1 is selected during application of the minor load to the test specimen. Gain G2 is utilized during testing on the standard B and C hardness scales, and corresponds to one hundred Rockwell hardness points per 0.2 mm displacement of the penetrator. Gain G3 is utilized during testing on the superficial N hardness scale and corresponds to 0.1 mm displacement per one hundred Rockwell hardness points. The analog output of amplifier 88 is also connected to a digital voltmeter 94 which provides at its output a bit-parallel signal to a digital display illustrated at 96 corresponding to the amplified and offset analog indication of penetrator displacement. The output of voltmeter 94 is also connected to a circuit 98 for detecting penetrator displacement during application of minor load within a preselected displacement limit range and for providing to control logic circuit 92 a limit signal LIM when penetrator displacement is in the selected range. The output of voltmeter 94 is also fed to a connector 100 for external use as by a printer or the like.

A precision voltage reference circuit 102 provides a reference input to digital voltmeter 94, and is also connected to a resistor network 104 comprising three adjustable resistors 106,108 and 110 connected in parallel between the reference voltage and ground. A rotary switch S1-A has fixed terminals C, B and N (corresponding respectively to selectable C, B and N hardness scales) connected to the wipers of resistors 106,108 and 110. The rotating contact 112 of switch S1-A is connected to one input of a comparator 114 which receives as a second input the analog output of amplifier 88. Comparator 114 provides a signal SCALE to control logic 92 which is at a high or logical one state when the comparator input from amplifier 88 is greater than that from switch S1-A, and which switches to a low or logical zero state when the inputs become equal. A second rotary switch S1-B has fixed terminals C, B and N connected to control logic circuit 92 and a rotating terminal 116 connected to electrical ground. Switches S1-A and S1-B are rotatably coupled and may comprise two decks and of a conventional rotary switch. A counter circuit 118, which may include a suitable oscillator and a digital up-counter, receives a count command signal from logic circuit 92 and provides a bit-parallel digital output to an analog-to-digital converter 120. Converter 120 receives a voltage reference signal from precision source 102 and provides an analog output to summing junction 86, which output is a direct linear function of the count in circuit 118. Control logic 92 has outputs respectively connected to indicator lamps 122,124 and 126 adjacent digital display 96 for signalling to an operator that a major load may be applied (122), that the applied major load may be removed (124), and that, upon completion of a test, the measured hardness is being displayed (126).

Operation of the invention will be explained with additional reference to FIG. 4, which is a state diagram functionally illustrating operation of control logic circuit 92, and FIG. 5 which illustrates ranges of displacement of the penetrator 10 and the corresponding numerical readings on digital display 96 during various modes of operation. The various control signals shown in FIG.

4 have been functionally identified hereinabove. The logical inverse of such signals in FIG. 4 means that the corresponding condition is not detected in the case of SP, LIM, MLA and DASH, or that the specified function is not being performed in the case of SCALE. For example, signal SP indicates that amplifier 80 detects presence of a sample, whereas $\overline{SP}$ means that no sample is detected. Signal SCALE illustrates that the inputs to comparator 114 are unequal and that the scaling operation must be performed, whereas the inverse $\overline{SCALE}$ means that the inputs are equal and the scaling operation may be terminated.

Initially it is assumed that the tester and the control logic circuit are in STATE 0 (FIG. 4). An operator places a test specimen 26 (FIG. 1A) on anvil 22, and then rotates lead screw 24 to raise the anvil and test specimen toward penetrator 10. When the test specimen engages the penetrator and lifts the penetrator from its rest position (FIG. 5) into the range 83, a sample present signal SP is fed by amplifier 80 to control logic 92 and the latter is stepped into STATE 1. In this state, selection circuit 90 is controlled to select an amplifier gain and offset G1 for displaying penetrator displacement during a first mode of operation, i.e., application of minor load. The test specimen and penetrator are displaced further by an operator against the downward force of minor load lever 14 and penetrator 10 until the displacement indicated at display 96 falls within a preselected numerical range corresponding to the penetrator minor load displacement range indicated at 128 in FIG. 5. The amount and range of penetrator displacement during application of minor load are selected based upon three considerations: (1) correct application of a minor load of desired magnitude (e.g., ten kilograms on the B and C scales) which occurs when lever arm 14 (FIG. 1A) is substantially horizontal; (2) the lower range limit must be such that the penetrator 10 and the LVDT core 72 will not be displaced during application of major load beyond the LVDT null position (see 134 in FIG. 5); and (3) upper range limit must be such that the minor load arm 14 does not abut major load lever screw 38. Minor load gain and offset factor G1 for amplifier 88 is selected such that the penetrator displacement 130 at the lower range limit will correspond to a numerical reading at display 96 of selected magnitude, preferably "100" in the present invention. Circuit components and tolerances are then selected such that the upper range limit 132 corresponds to an upper range numerical reading at display 96, preferably of "110". When the displacement falls within this range during the first or minor load mode of operation, circuit 98 (FIG. 1B) is activated. A minor load limit signal LIM is fed to logic circuit 98 which switches the logic circuit into STATE 2 (FIG. 4). In this state, lamp 122 (FIG. 1B) is activated to indicate to an operator that a major load may now be applied to the test sample.

The operator may then rotate handle 34 (FIG. 1A) which opens switch 62 and provides a signal MLA to the control logic circuit to initiate the second or major load mode of tester operation. Signal MLA indicates that application of the major load has been initiated and switches the control circuit into STATE 3. In STATE 3, the gain and offset of amplifier 88 are first altered either to gain G2 for hardness readings on the B or C scale as selected by switch S1-B, or to gain G3 for superficial hardness readings on the N scale. As is well known in the art, hardness is determined and measured by measuring total displacement of the penetrator after the major load has been applied and then removed using the penetrator position under minor load as a reference. Hence, a second operation must be performed in STATE 3 by means of which penetrator displacement and the resulting display at 86 during the second mode of operation are scaled to the particular hardness test scale selected by an operator. This function is performed by translating the position assumed by the penetrator during the first or minor load mode of operation into a numerical reference reading at display 96 corelated with and corresponding to the selected hardness scale.

More specifically, assume that a C hardness scale has been selected by switches S1-A and S1-B. Hardness number of the test specimen is then measured downwardly from a reference hardness number of "100" corresponding to the penetrator position after application of the minor load. For enhanced sensitivity, gain G2 is substantially higher than gain G1, such that switching from G1 to G2 forces the analog output of amplifier 88 to a level substantially higher than that in the first mode of operation in STATE 1. This higher level voltage is fed to comparator 114 which receives a reference signal from resistor 106 (the C hardness scale having been selected by switch S1-A). Resistor 106 is factory adjusted to yield a numerical display reading of "100" hardness numbers on the C scale at the minor load penetrator reference position. The analog signal from amplifier 88 is initially substantially higher than the reference level from resistor 106 and the SCALE output of comparator 114 is thus at a high level indicating to control logic 92 that the output of amplifier 88 must be scaled or translated downwardly. This is accomplished by enabling operation of counter circuit 118 which provides a progressively increasing analog signal via a/d converter 120 to summing junction 86. Since the summing junction is at the inverting input of amplifier 88, the increasing scaling signal from converter 120 results in a correspondingly decreasing or lowering of the amplifier output signal to comparator 114.

When such output signal has been lowered to a level corresponding to the factory adjusted setting of resistor 106, the output of comparator 114 switches to a zero state ($\overline{SCALE}$), and further operation of counter 118 is inhibited. At this level, the output of amplifier 88 to voltmeter 94 corresponds to a numerical reading of "100" regardless of the position of penetrator 10 within range 128. The output of a/d converter 120 to the summing junction remains at the scaled or translated level for the remainder of the hardness test. It will be appreciated that the afore described operations, which take place in STATE 3 of the control logic circuit, are accomplished very rapdily, i.e., in milliseconds, before any major load may be applied to the penetrator and thereby alter the minor load or reference position. Resistor 106 is factory adjusted to turn off comparator 114 and thereby terminate the automatic scaling operation when the analog output from amplifier 88 through voltmeter 94 corresponds to a numerical display at 96 of "100" hardness numbers. Similarly, resistors 108 and 110 are factory adjusted to yield scaled hardness numbers of "130" and "100" on the B and N scales respectively. Although it may be theoretically possible to eliminate resistor 110 and tie switch terminal N to terminal C (since the starting or reference hardness number "100" is the same for the C and N scales), provision of separate resistors has been found to be advantageous to accommodate minor circuit variations between gain G2

(C scale) and gain G3 (N scale), as well as other circuit parameters.

It will also be appreciated that the auto scaling operation just described alters the tester electronic operating parameters and display readings to correspond to a selected hardness scale. The actual penetrator position does not change during the scaling operation. Thus, if the penetrator were positioned at 130 (FIG. 4) during the first mode of operation, the total range of actual penetrator displacement for the C, B and N scales would be as at 134. It is preferable to operate the LVDT in only one direction from the null position during the actual testing operation. Thus, as previously mentioned and as graphically illustrated in FIG. 5, lower limit 130 must be such that the range 134 does not pass the null position. Range 136 illustrates possible penetrator displacement if the penetrator were positioned at limit 132 in the first mode of operation.

Switching of the output of comparator 114 to the zero state also steps control logic 92 from STATE 3 to STATE 4. In STATE 4, the tester is in a stand-by mode of operation while the major load is gradually applied to the test specimen by dashpot 40 over a period of four to five seconds as is conventional. Display 96 is blanked and lamp 122 is extinguished. When the major load has been fully applied and linkage 42 drops out of engagement with major load lever 32 as previously described, the DASH signal is supplied to control logic circuit 92 by switch 50 and switches the control logic into STATE 5 wherein the remove major load lamp 124 is illuminated. When the operator then removes the major load by rotating the handle 34 to its initial position and thereby depressing actuator 64, switch 62 is reclosed to indicate that the major load is no longer applied (signal MLA) and thereby to switch the control logic into STATE 6. In STATE 6 hardness display lamp 126 is illuminated. At the same time, a digital signal which corresponds to a numerical indication of penetrator position after application and removal of the major load is displayed at 96.

During application of a major load, the penetrator is displaced downwardly into the test specimen toward the LVDT null position (see FIG. 5). When the major load is removed, elasticity of the test specimen automatically displaces the penetrator upwardly to a final penetrator test position. Comparison of this final position to the minor load reference position indicates specimen hardness number. The automatic scaling feature of the invention combined with the selected gains G2 or G3 insures that, in any selected hardness scale, the numerical indication at 96 of final penetrator position is equal to the hardness number. The tester and control logic may be then returned to STATE 0 by lowering the anvil 22 until the penetrator is in the initial rest position, at which point amplifier 80 indicates that the sample is no longer present (signal $\overline{SP}$).

Control logic 92 also includes facility for automatically aborting further testing should the operator perform any one of the above-described manual functions incorrectly. Referring to FIG. 5, if the tester and control logic are in STATE 1 and an operator attempts to apply a major load by rotating handle 34 and thereby initiating signal MLA before a minor load limit signal LIM is received, the control logic switches to STATE 7 which detects an operator error, flashes display 96 at a numerical level of "188.8", for example, to indicate to an operator that an error has been detected, and aborts further testing. The operator may continue to apply the major load; however, no hardness number will result until the tester and control logic are returned to STATE 0 by lowering the anvil and test specimen to generate an $\overline{SP}$ signal. If the control logic is correctly stepped from STATE 1 to STATE 2 by a minor load limit signal LIM and the operator thereafter further displaces the test specimen either downwardly back below lower minor load limit 130 (FIG. 4) or further upwardly above upper minor load limit 132, the minor load limit signal is removed (signal $\overline{LIM}$) and the control logic switches from STATE 2 to STATE 7. Similarly, if the control logic is in STATE 4 and the operator attempts to remove the major load ($\overline{MLA}$) before full major load application is indicated (DASH), the control logical switches from STATE 4 to STATE 7. If the operator attempts to apply a major load while the control logic is in STATE 6, the MLA signal from switch 62 (FIG. 1A) switches the control logic from STATE 6 to STATE 7, and display 96 shows the flashing error signal rather than the measured hardness number. Lowering of the test specimen (signal $\overline{SP}$) returns the control logic to STATE 0 from any other state.

Various appropriate design schemes for control logic circuit 92 will be self-evident to persons skilled in the art in view of the detailed functional description previously set forth. Such circuit schemes may be readily designed and built using commercially available integrated circuits.

Although the present invention has been described in detail in connection with a presently preferred embodiment thereof, many alternatives, modifications and variations will suggest themselves to persons skilled in the art. For example, that particular facet of the invention embodied in electrical switch 50 (FIGS. 1A, 2 and 3) for yielding a positive indication of full major load application is readily adaptable for use with means for gradually applying the major load other than the dashpot 40. For example, some conventional testers include springs or motors for gradually lowering the major load lever onto the penetrator, either of which techniques may be modified to embody switch 50. This particular facet of the invention is an important advance over prior art techniques for indirectly implying application of the major load by use of a time delay circuit or the like since such prior art techniques are readily susceptible to significant error.

In a similar vein, other switch configurations may be utilized in place of switch 50. For example, linkage 42 may be pivotally mounted to rod 44 by insulating bushings and may have an electrical lead connected thereto. Major load lever 32 is connected to electrical chassis ground through pivot pin 16. Thus, linkage 42 and the electrical lead will be connected to ground through the lever arm until the major load is entirely assumed by the test specimen. Numerical indicia for minor load penetration limits 130 and 132 other than "100" and "110" may be utilized, gain G1 and the remaining circuit components being selected to yield any desired upper and lower display range. The limits of "100" and "110" have been selected and are preferred because they are considered to be easy for an operator to remember.

It will also be appreciated that the invention described herein is readily adaptable in its broader aspects to fully automated penetration hardness testing. For example, lead screw 24 may be connected to a stepping motor or the like and minor load limit detection circuit 98 connected to suitable stepping motor control circuitry for arresting motor rotation when the penetrator moves within the minor load displacement range. Similarly, a solenoid or the like may replace manual major load lever 34 (FIG. 1A), and may be controlled to apply the major load in STATE 2 (FIG. 4) of the control logic and remove the major load in STATE 5. The present invention is intended to embrace the foregoing and all other alternatives, modifications and variations as fall within the spirit and broad scope of the appended claims.

The invention claimed is:

1. In a penetration hardness tester which includes a penetrator, lever means carrying a load adapted to be applied to said penetrator, linkage means operatively coupled to said lever means and means connected to said linkage means for gradually lowering said lever means onto said penetrator, the improvement comprising switch means coupled to said lever means and said linkage means for directly indicating application of the entire load carried by said lever means to said penetrator.

2. In a penetration hardness tester which includes a penetrator, lever means carrying a load adapted to be applied to said penetrator, linkage means operatively coupled to said lever means and means connected to said linkage means for gradually lowering said lever means onto said penetrator, said linkage means being disposed to support said lever means as said lever means is lowered onto said penetrator, after which said linkage means is adapted to descend further out of supporting contact with said lever means, the improvement comprising switch means operatively coupled to said lever means and said linkage means and responsive to separation of said lever means and said linkage means for indicating application of the entire load carried by said lever means to said penetrator.

3. The improvement set forth in claim 2 wherein said lever means is disposed to pivot in a vertical plane and said penetrator is disposed below said lever means, and wherein said linkage means is supportingly coupled to said lever means for gradually descending and thereby lowering said lever means onto said penetrator.

4. The improvement set forth in claim 2 wherein said switch means includes an electrical switch carried by said lever means and having a downwardly projecting switch actuator normally engaged by said linkage means.

5. The improvement set forth in claim 4 wherein said lowering means comprises a dashpot disposed above said lever means, and wherein said linkage means includes means coupled to said dashpot and extending beneath said lever means for lowering said lever means against the restraining force of said dashpot by force of gravity.

6. A penetration hardness tester for providing a digital reading of specimen hardness number measured in a predetermined hardness scale comprising penetration means including load means adapted to be coupled to said penetration means, anvil means for carrying a test specimen, means adapted in a first mode of operation for displacing said anvil means and a test specimen against said penetration means to apply a minor load of desired magnitude through said penetration means to the specimen, digital display means, and circuit means coupled to said penetration means and said display means for providing at said display means a numerical indication of displacement of said penetration means from a rest position, said circuit means including means operable in said first mode of operation for relating said display means to displacement of said penetration means such that a digital reading of said display means within predetermined numerical limits indicates application of said desired minor load to said penetration means and test specimen.

7. The tester set forth in claim 6 wherein said penetration means further comprises means adapted in a second mode of operation to apply a major load of desired magnitude through said penetration means to the test specimen, and wherein said circuit means further comprises means for automatically inhibiting said display means from providing said hardness number in said second mode of operation when said displacement of said penetration means is outside of said predetermined numerical limits in said first mode of operation.

8. The tester set forth in claim 7 further comprising means adapted to switch said tester from said first mode of operation to said second mode of operation, and wherein said inhibiting means includes first means responsive in said first mode of operation to displacement of said penetration means exceeding said limits to inhibit said display and second means responsive to said switching means and to displacement of said penetration means below said preselected limits to inhibit said display means.

9. The tester set forth in claim 8 wherein said inhibiting means includes means responsive to return of said penetration means to said rest position for re-enabling operation of said tester in said first mode of operation.

10. The tester set forth in claim 6 wherein said penetration means further comprises means adapted in a second mode of operation to apply a major load of desired magnitude through said penetration means to said test specimen and means for switching said tester from said first to said second mode of operation, and wherein said circuit means further comprises means responsive to said switching means and operable in said second mode of operation for scaling displacement of said penetration means in said second mode of operation to said predetermined hardness scale.

11. The tester set forth in claim 10 wherein said penetration means is disposed at a first position upon application of said minor load as indicated by said digital reading within said preselected numerical limits, and wherein said scaling means comprises means for automatically translating said first position reading into a reference reading corresponding to said predetermined hardness scale.

12. The tester set forth in claim 11 further comprising means for selecting either the B or the C hardness scale, and wherein said scaling means includes means responsive to said scale selecting means for translating said first position reading into a reference reading of 100 when said C scale is selected and into a reference reading of 130 when said B scale is selected.

13. The tester set forth in claim 12 further comprising means for selecting an N superficial hardness scale, and wherein said scaling means further includes means for translating said first position reading into a reference reading of 100 when said N scale is selected.

14. A penetration hardness tester for providing a reading of specimen hardness number measured in a predetermined hardness scale comprising penetration means including load means adapted to be coupled to said penetration means, anvil means for carrying a test specimen, means adapted in a first mode of operation for applying a minor load of desired magnitude through said penetration means to a specimen, means adapted in a second mode of operation for applying a major load of desired magnitude to the test specimen, means for switching from said first to said second mode of operation, numerical display means, and circuit means coupled to said penetration means and to said display means for providing at said display means a numerical indication of displacement of said penetration means, said circuit means including means operable in said first mode of operation for measuring displacement of said penetration means to a first position and means operable during said second mode of operation for scaling further displacement of said penetration means in correlation with said predetermined hardness scale by translating measured displacement at said first position into a numerical reference reading at said display means corresponding to said predetermined hardness scale.

15. The tester set forth in claim 11 or 14 wherein said circuit means includes means for providing an analog first signal as a function of displacement of said penetrator means and amplifier means for receiving said first signal and providing an analog output signal to said display means, and wherein said scaling means comprises means operable in said second mode of operation for varying the operating characteristics of said amplifier means until said output signal at said first position of said penetration means is at a level corresponding to said reference reading.

16. The tester set forth in claim 15 wherein said amplifier means includes variable offset means, and wherein said scaling means includes means coupled to said offset means for varying amplifier offset until said output signal is at said level corresponding to said reference reading.

17. The tester set forth in claim 16 wherein said circuit means further comprises summing means at an input of said amplifier means, and wherein said scaling means and said first signal means are connected to said summing means.

18. The tester set forth in claim 17 wherein said scaling means comprises means for generating a reference signal corresponding to said predetermined hardness scale, means for comparing said output signal to said reference signal, a digital counter including means for stepping said counter when said output signal is unequal to said reference signal, and analog-to-digital converter means coupling said counter to said summing means.

19. The tester set forth in claim 18 adapted to measure hardness on a plurality of selectable hardness scale wherein said reference signal generating means includes means for generating a reference signal corresponding to each selected hardness scale.

20. A semiautomatic penetration hardness tester for measuring specimen hardness number measured in a predetermined hardness scale comprising penetration means including a penetrator, minor load means coupled to said penetrator and major load means adapted to be selectively coupled to said penetrator, an anvil for carrying a test specimen, means including a lead screw coupled to said anvil and adapted in a first mode of operation for manually raising a test specimen against said penetrator and minor load means, manual means for switching from said first mode of operation to a second mode of operation wherein said major load means is coupled to said penetrator, circuit means for providing a signal indicative of displacement of said penetrator, visual display means responsive to said signal for displaying to an operator displacement of said penetrator during said first mode of operation and hardness number during said second mode of operation, and means automatically responsive to displacement of said penetrator in a first mode of operation during manual application of said minor load to inhibit display of said hardness number in said second mode of operation when displacement in said first mode of operation falls outside of a preselected limit range.

21. The tester set forth in claim 20 wherein said means for switching from said first to said second mode of operation includes an operator responsive handle, and wherein said circuit means includes electrical switch means disposed to detect movement of said handle.

22. The tester set forth in claim 21 wherein said inhibit means includes first means responsive in said first mode of operation to said displacement exceeding said preselected limit range and second means responsive to said electrical switching means and to failure of said displacement to reach said preselected limit range.

23. The tester set forth in claim 20 further comprising indicator means responsive to displacement within said preselected range for indicating to an operator that a major load may be applied.

24. The tester set forth in claim 23 further comprising first means for sensing application of a major load and means responsive to said sensing means for indicating to an operator that said major load may be removed.

25. The tester set forth in claim 24 further comprising second means for sensing removal of said major load and means responsive to penetrator displacement to said second means for indicating completion of a test.

26. The tester set forth in claim 25 further comprising means responsive to said second means and to said sensing means in said second mode of operation to inhibit said display of said hardness number.

27. The tester set forth in claim 24 wherein said means for applying a major load comprises major load lever means, linkage means disposed beneath said lever means for supporting said lever means and means coupled to said linkage means for gradually lowering said lever means, and wherein said sensing means include electrical switch means responsive to separation of said linkage means and said lever means when said major load is fully applied to said penetrator.

28. The tester set forth in claim 20 wherein said display means comprises digital display means.

* * * * *